(12) United States Patent
Paternostro et al.

(10) Patent No.: US 10,095,842 B2
(45) Date of Patent: Oct. 9, 2018

(54) METHODS FOR ARTIFICIAL COMBINATORIAL CONTROL OF BIOLOGICAL SYSTEMS

(75) Inventors: Giovanni Paternostro, Del Mar, CA (US); Jacob D Feala, Washington, DC (US)

(73) Assignee: SALGOMED, INC., Del Mar, CA (US)

( * ) Notice: Subject to any disclaimer, the term of this patent is extended or adjusted under 35 U.S.C. 154(b) by 401 days.

(21) Appl. No.: 13/118,395

(22) Filed: May 28, 2011

(65) Prior Publication Data

US 2012/0015834 A1    Jan. 19, 2012

Related U.S. Application Data

(60) Provisional application No. 61/349,750, filed on May 28, 2010.

(51) Int. Cl.
*G06F 19/00* (2018.01)
*C40B 50/02* (2006.01)
*G06F 19/12* (2011.01)

(52) U.S. Cl.
CPC ............ *G06F 19/706* (2013.01); *C40B 50/02* (2013.01); *G06F 19/12* (2013.01)

(58) Field of Classification Search
None
See application file for complete search history.

(56) References Cited

U.S. PATENT DOCUMENTS

| | | | |
|---|---|---|---|
| 6,372,185 B1 * | 4/2002 | Shumate | B01J 19/00 422/510 |
| 8,168,568 B1 * | 5/2012 | Mehta et al. | 506/10 |
| 2011/0191868 A1 * | 8/2011 | Gupta et al. | 800/8 |

OTHER PUBLICATIONS

Calzolari et al, PLoS Computational Biology, 2008, 4:12, e1000249.*

* cited by examiner

*Primary Examiner* — Larry D Riggs, II
(74) *Attorney, Agent, or Firm* — Wagenknecht IP Law Group PC

(57) ABSTRACT

Methods and systems for determining a set of control molecules for use in a combinatorial approach for the treatment of medical conditions, including providing one or more sets of control molecules, where each control molecule within the set acts on a set of targets and the number of control molecules within the one or more sets of control molecules is fewer than the number of targets within the sets of targets; and searching within the sets of control molecules to identify a subset of control molecules that together with a subset of targets form an artificial system to produce a biological effect through the modulation of the subset of targets.

15 Claims, 8 Drawing Sheets

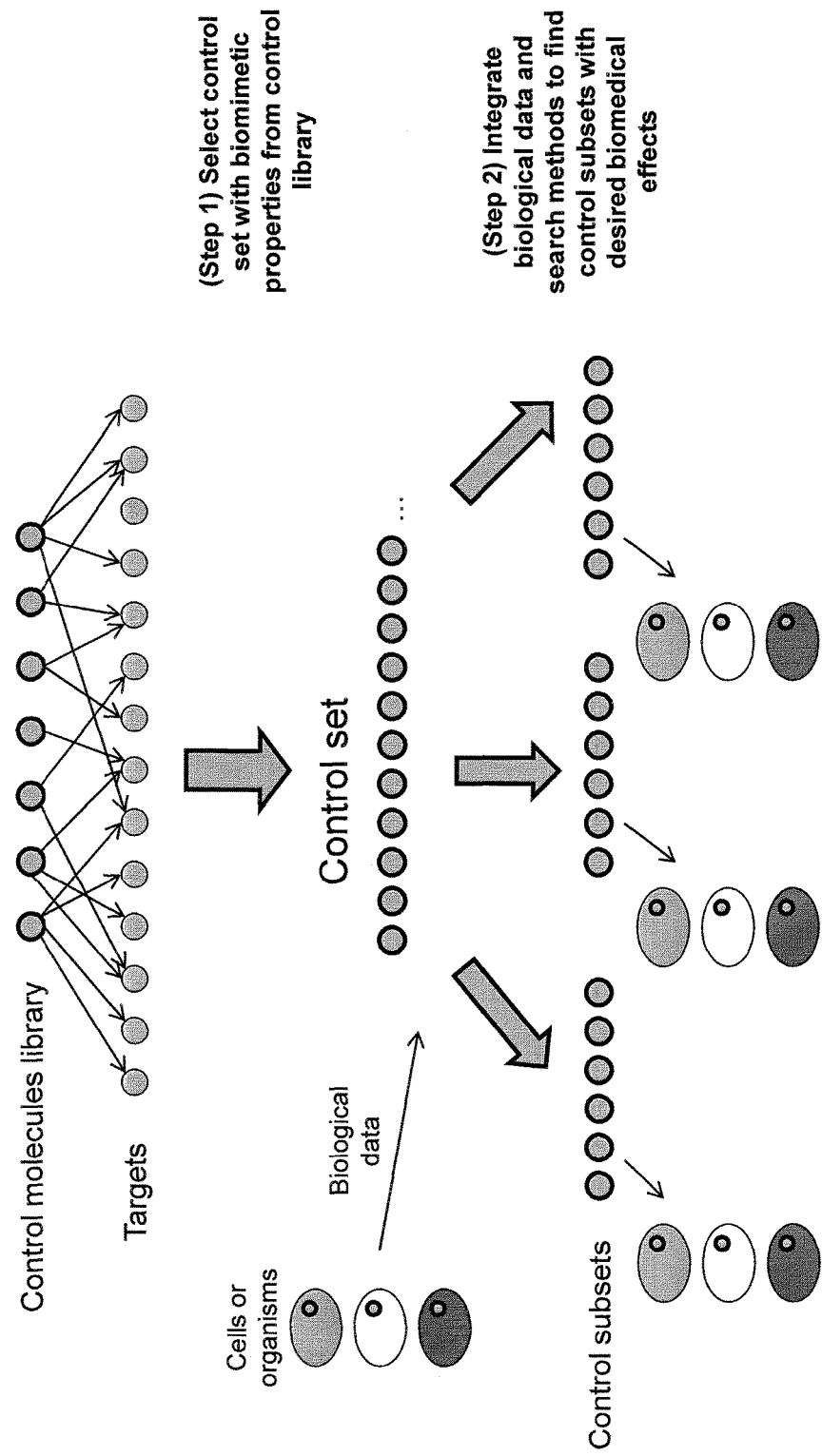

FIG. 5

Table 1

|  |  | Literature | | | Network databases | | | | | | |
|---|---|---|---|---|---|---|---|---|---|---|---|
|  |  | Human | | | Human | | | Yeast | | E. coli | Drug |
|  |  | TF | Kinase | miRNA | TF | Kinase | miRNA | TF | Kinase | TF | KI |
| Node properties | | | | | | | | | | | |
| | Controllers (M) | 1,800 | 518 | 940 | 389 | 264 | 153 | 186 | 88 | 169 | 38 |
| | Targets (N) | 20,500 | 6,150 | 11,890 | 9284 | 988 | 9448 | 6297 | 1341 | 1495 | 316 |
| | M/N (%) | 8.8% | 8.4% | 7.9% | 4.2% | 26.7% | 1.6% | 3.0% | 6.6% | 11.3% | 12.0% |
| Link properties | | | | | | | | | | | |
| | Targets per controller (mean) | | | | 18.1 | 8.9 | 35.9 | 22.9 | 4.6 | 20 | 78.8 |
| | Controllers per target (mean) | | | | 7.6 | 2.4 | 5.8 | 6.8 | 3 | 2.3 | 9.48 |
| | Link density | | | | 1.9% | 0.9% | 3.5% | 3.6% | 3.5% | 1.3% | 25.0% |
| | Shared targets per controller (mean) | | | | 98% | 73% | 95% | 98% | 85% | 74% | 100% |
| | Pairwise overlap of targets (mean) | | | | 4.5% | 7.1% | 7.1% | 6.3% | 8.3% | 1.1% | 33.6% |

Statistical values of selected parameters

| Parameter | Mean | SD | CV | 95% lo | 95% hi |
|---|---|---|---|---|---|
| M/N (literature) | 8.4% | 0.5% | 0.054 | 7.5% | 9.3% |
| Controllers per target | 4.7 | 2.4 | 0.51 | 0.016 | 9.3 |
| Link density | 2.5% | 1.2% | 0.50 | 0.041% | 4.9% |
| Shared targets per controller | 87.2% | 11.6% | 0.13 | 0.6% | 10.8% |
| Pairwise overlap of targets | 5.7% | 2.6% | 0.45 | | |

METHODS FOR ARTIFICIAL COMBINATORIAL CONTROL OF BIOLOGICAL SYSTEMS

CROSS REFERENCE TO RELATED APPLICATIONS

This invention claims benefit of priority to U.S. Patent Application Ser. No. 61/349,750, filed on May 28, 2010; the contents of which are herein incorporated by reference in their entirety.

TECHNICAL FIELD

The invention relates to combinatorial analysis of biological systems and more specifically to methods for determining a set of compound molecules that modulate a set of endogenous target molecules to produce a beneficial biomedical or biological effect.

BACKGROUND ART

Control of cellular function depends on bipartite networks, in which one class of nodes (the controller) acts on the other class (the target) to regulate its function. Examples of cellular control networks include transcription factors, microRNAs, and protein kinases (1). In these networks, the control layer interacts with the target layer in a combinatorial, "many-to-many" fashion (see FIG. 1). In other words, each controller has many targets, the targets themselves are under the influence of many controlling molecules, and the target sets of different controllers overlap. Moreover, the number of controllers is usually significantly lower than the number of targets. While this is well recognized in biological systems, and the control problem in natural systems has been studied using simple models, for example, using Boolean networks, design principles of biological control are still not well understood. This lack of understanding also limits our ability to design more natural modes of multi-agent biological intervention. The network principles of combinatorial control in biology may serve as a guide to more effective combinatorial targeting patterns in combinatorial therapies, differentiation factors, and other modes of artificial control of biological systems.

Examples of Many-to-Many Control in Biology

A many-to-many combinatorial structure is not limited to the control of cells and it is found in all types of complex control in biology, the most striking example being the control of the organism by the nervous system, where connections among neurons have a many-to-many arrangement. The control of effectors by neurons has a simpler structure, as shown by motor units, where each motor neuron controls a distinct set of muscle fibers and the target sets are not overlapping, in a one-to-many fashion. The complexity of control structure might depend on the complexity of the target system.

Diseases such as cancer may also adapt by developing combinatorial strategies to counter intrinsic defense mechanisms and homeostatic reactions or extrinsic therapeutic interventions. An increasing body of evidence shows that the resistance of cancer to therapies involves molecules acting at multiple levels with many-to-many actions. This provides further support for the use of biomimetic therapeutic strategies of matching complexity.

Although combinatorial strategies to treat medical conditions have been proposed, there remains a need to effectively identify suitable therapeutic combinations of control molecules to modulate a plurality of endogenous molecules thereby producing desired biological effects.

Combinatorial Therapies

Recent development in the field of combinatorial therapies have been reviewed in (2). It is becoming increasingly evident to the clinician treating a complex disease or to the scientist studying a complex biological network that accurate control is more likely to be achieved by using multiple interventions. Since therapeutic molecules are increasing in specificity (as in the case of targeted drugs), and since our knowledge of the complexity of biological networks is advancing, it is becoming more feasible to consider drugs not as remedies for specific disorders but rather as a kit of molecular tools that can be combined for specific therapeutic purposes.

Because drug effects are dose-dependent, several doses need to be studied and, when therapeutic interventions on multiple targets are necessary, the number of possible combinations rises very quickly (this problem is often referred to as combinatorial explosion). For example, if we were to study all combinations of 6 out of 100 compounds (including partial combinations containing only some of these compounds) at 3 different doses we would have $S^6_{j=1}$ Binomial$(100,j)*3^j=8.9*10^{11}$ possibilities. This example suggests that the problem will require a qualitatively new approach rather than more efficient screening technology alone. Many cancer chemotherapy regimens are composed of 6 or more drugs from a pool of more than 100 clinically used anticancer compounds.

The traditional approach to combination therapy has been called empirical (3, 4) rather than systematic. A common assumption in the empirical approach is that only drugs that are effective individually should be used as part of a drug combination (5).

The limitations of this traditional approach to drug combinations have been described in a Commentary in The New England Journal of Medicine (6). Other reviews stressing the need for a more systematic approach to combination therapy have been published by Dancey and Chen (7), Hopkins (8) and Zimmerman et. al. (9). An editorial (3), commenting on the disappointing results of a clinical trial of combination therapy for colorectal cancer (10), suggested that combining the new targeted therapies might be even more challenging than combining cytotoxic chemotherapies, because of subtle interactions in intracellular signaling.

SUMMARY OF THE INVENTION

The invention provides methods and systems for determining a set of control molecules for use in a combinatorial approach for the treatment of medical conditions and provides related benefits. The above is accomplished through the development of a method for determining a subset of control molecules capable of artificial combinatorial control of a biological system to produce a biological effect, and a medium for storing information to permit a computer based-system to execute the method.

The method includes providing one or more sets of control molecules, where each control molecule within the set acts on a set of targets. At least some sets of targets partially overlap one another by sharing one or more targets between control molecules. In some embodiments the overlap is between 0.1% and 10%. The number of control molecules within the one or more sets of control molecules is fewer than the number of targets within the sets of targets. In some embodiments the size of the subset of control molecules, as a percentage of the target set, is between 0.3 and 10. In other embodiments, the size of the one or more sets of control molecules, as a percentage of the target set, is between 0.5 and 20.

In some embodiments, the set of targets includes a majority or all members of a class of signal transduction or regulatory molecules. In some embodiments the set of targets is selected from the group consisting of a set of protein kinases, protein phosphatases, proteases, microRNAs, and metabolic enzymes. Exemplary control sets include those selected from the group consisting of microRNAs, small molecules, peptides, proteins, cytokines and metabolites.

The one or more sets of control molecules are searched to identify a subset of control molecules that together with a subset of targets form an artificial system to produce a biological effect through the modulation of the subset of targets. The number of interactions between the control molecules and the targets, as a percentage of all possible interactions between control molecules and targets, is between 0.1 and 10. In some embodiments, the number of control molecules per target molecule follows a monotonically decreasing distribution, optionally comprising an exponential or power-law distribution.

Searching may include performing an algorithm, such as a stack sequential algorithm or a sequential decoding algorithm. Exemplary systems that may be searched include a living cell in an in-vitro culture, a computational representation of a biological system, and an organism. Among the assays or indications that may be searched include growth, survival, or death of a living cell or organism, expression of an mRNA transcript or encoded protein, obtaining a concentration of a predetermined metabolite or set of metabolites, differentiation of one cell type to another cell type and expression of a surrogate marker for therapeutic effect.

BRIEF DESCRIPTION OF THE DRAWINGS

FIG. 2 depicts a set of graphs showing distributions of links per node k, for incoming links (controllers per target, $k_{in}$) and outgoing links (targets per controller, $k_{out}$).

FIG. 3 depicts a schematic showing an overview of the technical approach taken by the invention.

FIG. 5 depicts a table (Table 1) showing exemplary network parameters for various types of combinatorial control within cells (1). The ratio of controllers per target drawn from the literature is similar across different types of biological network in humans, approximately 8%. Node properties differ between the literature and network databases owing to incomplete information in the databases. Link density is the ratio of the number of actual links to the number of possible links. Shared targets per controller and pairwise overlap are measurements of overlapping target sets described in the supplementary material. SD=standard deviation, CV=coefficient of variation.

DETAILED DESCRIPTION

A. Definitions

Figure 1:
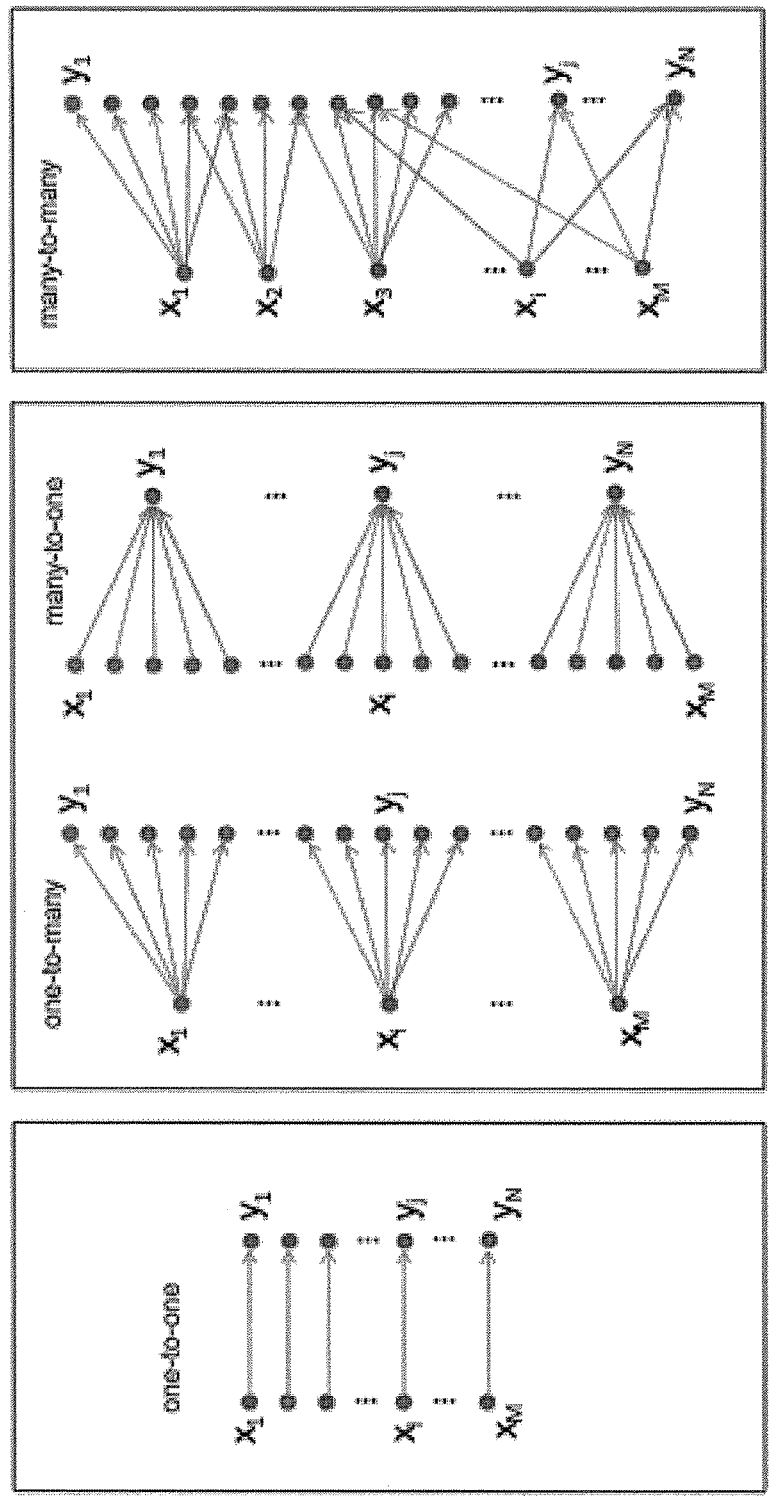
FIG. 1 depicts a graph showing four control strategies between controllers and targets, namely one-to-one, one-to-many, many-to-one, and many-to-many.

The term "combinatorial" as used herein refers to multiple entities, such as multiple control molecules.

The term "control molecule" as used herein refers to a drug or other agent that modulates a target molecule to induce a biological effect. Control molecules are often provided in a group or set, termed "control set" or "set of control molecules." A control molecule is also referred to as a "controller." A "control subset" refers to a group control molecules identified from the set of control molecules which induces the desired biological effect. Control molecules can have multiple targets and thus result in multiple biological effects. The term "combinatorial control" as used herein refers to obtaining a biological effect using multiple control molecules to modulate multiple targets.

The term "target" as used herein refers to an endogenous biological molecule with which a control molecule interacts to induce a biological effect. A "target" is modulated by a control molecule. A "set of target molecules" is the initial grouping of targets. A "subset of target molecules" refers to a selection of targets from the set of targets that interact with the subset of molecules to provide the desired biological effect.

The term "class of targets" as used herein refers to a type of molecularly and functionally distinct targets such as a class of signal transduction or class of regulatory molecules, more specifically such as kinases or mRNA molecules.

The term "modulate" or "modulation" as used herein refers to an increase or decrease in biological activity. A control molecule modulates a target molecule.

The term "interaction" as used herein refers to the relationship between a control molecule and a target molecule, which may include a regulatory relationship or binding relationship.

The term "biomimetic" as used herein refers to possessing one or more features similar to those found in biology. An example of a "biomimetic" is many-to-many control.

The term "many-to-many" as used herein refers to a type of structure of a relationship among control molecules and targets (see FIG. 1, right end panel) where each controller acts on many targets, each target has many controllers and the sets of targets of different controllers are partially overlapping.

The term "partial overlap" as used herein refers to the situation in which two control molecules act on some, but not all, of the same target molecular species.

The terms "network parameters" or "network characteristic" as used herein refer to mathematical properties of the network of molecular interactions, such as those commonly used in the field of graph theory to describe features of a set of nodes and links.

The term "node" as used herein refers to a component within the molecular network, representing a particular biomolecular species or sequence.

B. Introduction to Combinatorial Therapies and Interventions

The evolutionarily conserved nature of the many-to-many structure, certain measured network parameters, and the exponential distribution of links suggests that pharmacological control strategies should be designed similarly. This represents a divergent approach from current efforts to develop specific, targeted therapies which follow the one-to-one approach to drug therapy (11, 12); in other words, the ideal aim of drug discovery is seen as having one drug for each molecular target, with no target overlap. Other traditional therapies are often less specific (one-to-many in FIG. 1) and some effective targeted therapies have also been found to be non-specific and might fit this category (13, 14).

Biomimetic control sets are sets of control molecules (for example drugs or biologicals) for designing combinatorial therapies or interventions, with similar structure and parameters as the biological control systems. These control sets can be used to search for control subsets with desired biomedical effects, such as the modulation of one or more biological pathways. As such, the control subsets can be used to selectively enhance some biological activities while inhibiting others. Desired biomedical effects are induced through the modulation of target molecules via control molecules. As such, determining desirable control molecules or desirable subsets of control molecules may be performed by identifying a set of target molecules believed to be associated with the medical condition, identifying a set of control molecules that modulate the set of target molecules and determining which combination(s) of control molecules within the set provides the most efficient modulation of target molecules. In general, desired subsets of control molecules will include at least some control molecules that act on at least two, but preferably more than two target molecules.

Identifying suitable target molecules may be performed by screening databases that correlate presence, abundance, absence, activity and the like of biological molecules with regard to for the medical condition or biological process of interest. For instance, National Cancer Institute (NCI) regularly provides biological samples from those suffering from a variety of cancer conditions and stages. These samples are studied for abundance, absence or indications of activity for a variety of polypeptides, nucleic acids and the like. As such, a variety of databases accessible by computer provide information regarding differentially expressed polypeptides, cancer related genes and the like. Examples of targets that are of interest include protein kinases, protein phosphatases, proteases, microRNAs, metabolic enzymes, regulatory molecules, signal transduction molecules and the like. Still further, databases provide a source of control molecules within a control set by obtaining information regarding small molecules, organic compounds, polypeptides, small peptides and the like such as those believed to enzyme inhibitors, such as kinase inhibitors and protease inhibitors, transcription factors and the like. Control molecules known or believed to modulate targets may be used within a set of control molecules. That is the skilled artisan can obtain connectivity data between sets of control molecules and sets of target molecules from reported studies for use in the methods to determine a desirable control subset.

Alternatively, one skilled in the art may undertake the process of performing experiments such as determining differential expression of polypeptides, genes and the like to identify targets for inclusion in a set of targets and may perform experiments to assess protein expression, gene activation and the like to identify control molecules for inclusion in a set of control molecules for determining desirable control subsets.

Accordingly, one use of control subsets is that of combinatorial therapies for groups of patients with the same disease by providing or emphasizing target molecules that are found within the groups of patients. These combinations might also be optimized further for individual patients by consideration of target molecules or sets of target molecules differentially found in the individuals. This is similar to what nature achieves by expressing subsets of regulatory molecules from the set encoded in the genome, in order to achieve different cell types or phenotypic states. For example, only a subset of transcription factors, microRNAs and protein kinases are expressed in a given cell type, and these are sufficient to determine the state of the system.

The percentage of expressed genes and controllers can be used to estimate the size range of the control subsets. See FIG. 3 for a scheme of this procedure.

The most general biomimetic property of control sets is the many-to-many relationships among controllers and targets (see FIG. 1, right end panel). Other quantitative parameters and distributions of controllers and target structures used in nature are shown in FIG. 5 (Table 1) and in FIG. 2. Among these parameters are the average numbers and distributions of controllers per targets and targets per controller. A mathematical model we have developed (1) explains, at least in part, the reason for the particular values of some of these parameters. These parameters and distribution are used to obtain the control set, starting from a library of controllers with known targets. In some applications, information about the targets present in the biological system to be controlled can be used in the design of the control set. See FIG. 3, step 1.

We can then use experimental search algorithms, for example those previously described by us and by other groups for searches within drug libraries, to identify control subsets with desired biological or biomedical effects. The search algorithms can also use information from statistical and mechanistic models and from other biological data, including omic data (genomic, transcriptomic and proteomic), to help guide the search. The control subsets can also have biomimetic properties, as the many-to-many structure. See FIG. 3, step 2. From the data, further analysis properties is achieved such as through determining density of links, distribution of links for each type of node and overlap between the target sets of different controllers.

The skilled artisan will appreciate the search algorithm and strategy may search results from a variety of endpoint assays, which may also be ordered in importance. That is, a variety of assays are available to the skilled artisan revealing pertinent information regarding biological systems. Among these include those to assess growth, survival, or death of a living cell or organism, expression of an mRNA transcript or encoded protein, obtaining a concentration of a predetermined metabolite or set of metabolites, differentiation of one cell type to another cell type, expression of a surrogate marker for therapeutic effect and the like.

This approach to pharmacology has a modular design, as in biological control, and is therefore more efficient than the present practice of developing a different drug for each indication, because the same sets of molecules can be used to search for therapies for different complex diseases (e.g., for cancer and for inflammation).

It is important to note that the quantitative properties of the control sets cannot be described simply by analyzing properties of individual drugs. The fundamental unit of pharmacological control for complex diseases could be the biomimetic control set and not the individual drug.

C. Technical Approach to Combinatorial Analysis to Identify Control Molecules for Use in Artificial Systems As an exemplary embodiment to demonstrate the technical approach taken by the methods we examine quantitative characteristics of these three biological control systems in three different species (human, yeast, and *E. coli*), from the perspective of two-layer combinatorial control. First we consider the numbers of nodes. FIG. 5 (Table 1) shows estimates of the number of controllers and targets from the literature for the three types of networks in humans. Notably, though these numbers are from three different cellular systems of varying size, the ratios of control nodes to target nodes are similar, approximately 8%.

Next, we use molecular interaction databases to explore connectivity parameters of bipartite networks in nature. Networks were extracted from publicly available databases and separated into controller nodes (microRNA, transcription factors, protein kinases) and target nodes (mRNA transcript, gene, phosphorylated protein substrate), with directed links between controllers and targets. We also used existing protein kinase target profiles for a set of kinase inhibitors (15) (KIs), for comparison with the endogenous networks. While there have been many genome-wide network analyses (16-21), and one recent work on co-regulation of transcription and phosphorylation networks (22), here we focus on universal features of bipartite networks that may help design biomimetic control strategies. We quantified properties including density of links (existing links divided by the number of possible links), distribution of links for each type of node, and overlap between the target sets of different controllers. Where possible, we gauged the biological significance of these features by comparison with those expected from a random network having the same number of nodes and links. Deviations from random may indicate a functional advantage for a particular network characteristic.

Figure 2A:
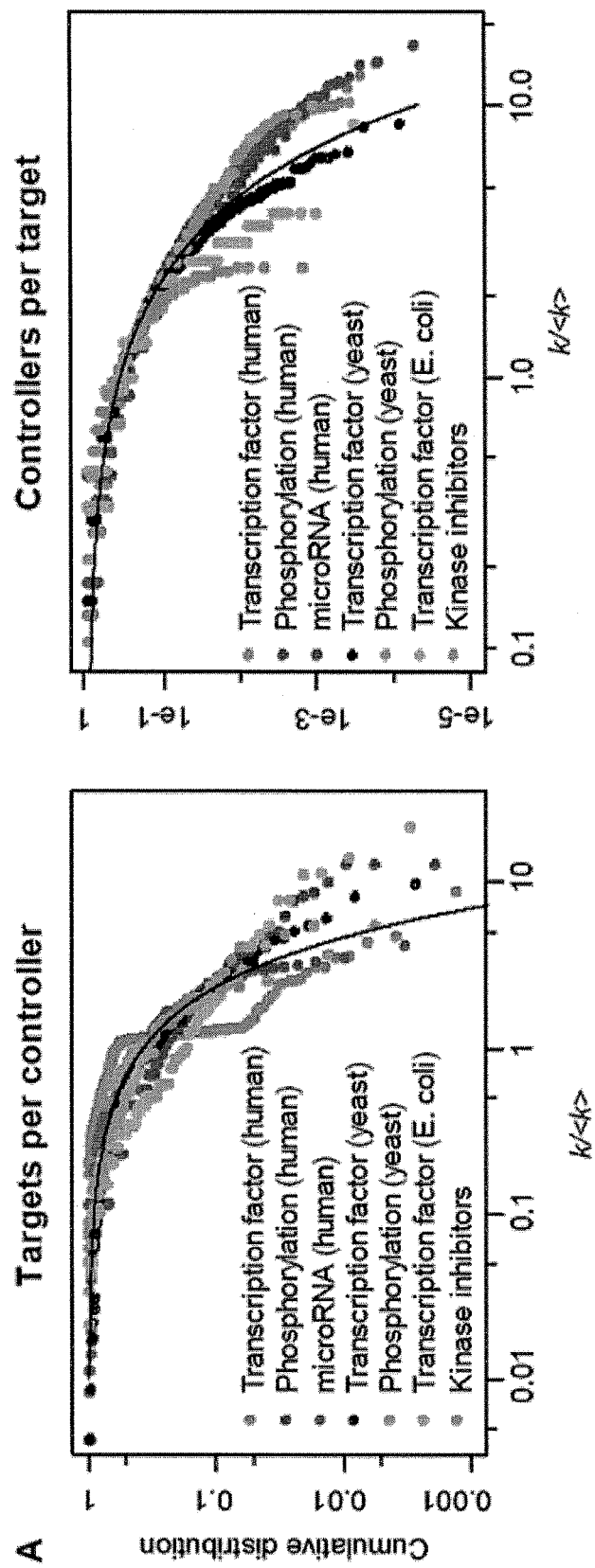
FIG. 2A depicts the empirical cumulative distribution function (cdf) for all datasets, normalized by the average links per node <k> and overlaid on a standard exponential cdf (solid line).
Figure 2B:
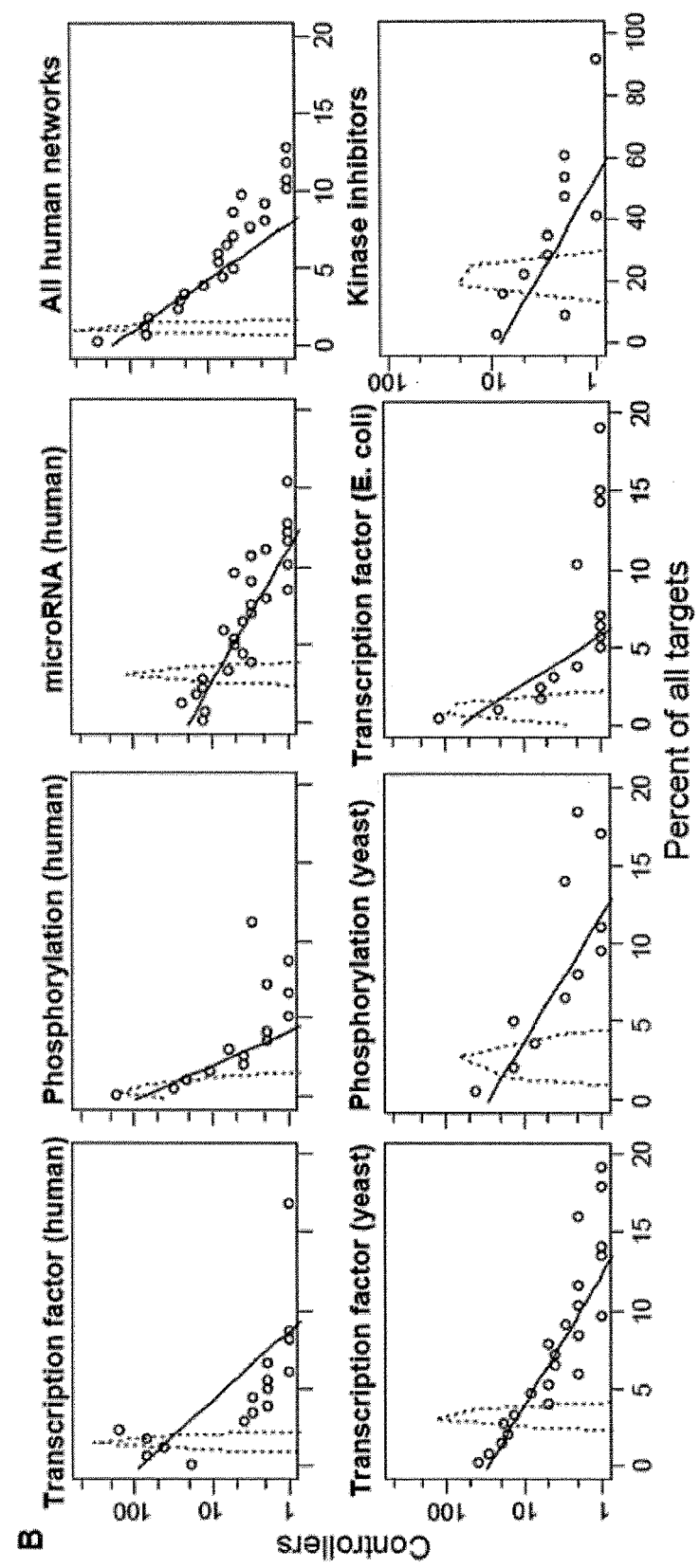
FIGS. 2B and 2C show histograms of each individual network, compared with the binomial distributions expected of random networks of the same size generated by the Erdös-Rényi random graph model.
Figure 2C:
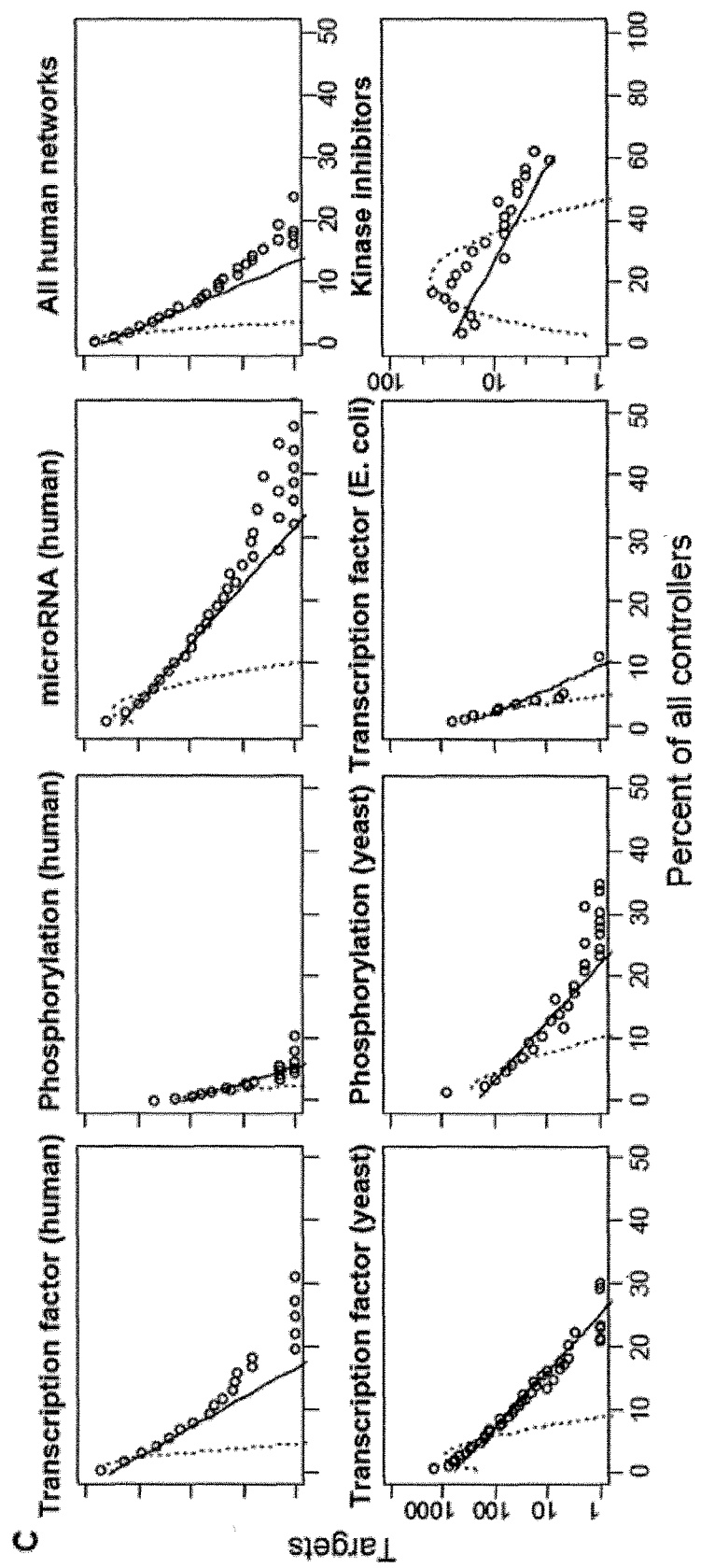

FIG. 2 shows distributions of links per node k, for incoming links (controllers per target, kin) and outgoing links (targets per controller, kout). FIG. 2A depicts the empirical cumulative distribution function (cdf) for all datasets, normalized by the average links per node <k> and overlaid on a standard exponential cdf (solid line). FIGS. 2B and 2C show histograms of each individual network, compared with the binomial distributions expected of random networks of the same size generated by the Erdös-Rényi random graph model (23). The human transcription factor network has a peak in its outgoing link distribution that is accurately approximated by a binomial distribution. The incoming links in the kinase inhibitor network also show a possible binomial component. Otherwise, most curves approximate an exponential distribution.

All biological networks had similar sparse link density, realizing an average of only 2.5%±1.2% of all possible controller-to-target interactions. Link density D is related to the average links per node by the equation $$D = \frac{\langle k_{in} \rangle}{M} = \frac{\langle k_{out} \rangle}{N}, \qquad (1)$$

where $\langle k_{in} \rangle$ is the average incoming links over N target nodes, and $\langle k_{out} \rangle$ is the average outgoing links from M controller nodes. Note that $$\frac{\langle k_{in} \rangle}{\langle k_{out} \rangle} = \frac{M}{N}, \qquad (2)$$

suggesting that similarities in the ratios of nodes may be related to constraints on the average incoming and outgoing links per node.

D. Computer Based Systems

The invention also provides software and instructions for performing the above methods on a computer readable medium executable by one or more processing devices, such as computer systems. In an exemplary embodiment the computer-readable medium stores instructions executable by one or more processing devices to perform a method of finding optimized combinatorial therapies, the method including: a) providing one or more sets of control molecules, wherein each control molecule within the set acts on a set of targets, wherein at least some sets of targets partially overlap one another by sharing one or more targets, further wherein the number of control molecules within the one or more sets of control molecules is fewer than the number of targets within the sets of targets; and b) searching within the one or more sets of control molecules to identify a subset of control molecules that together with a subset of targets form an artificial system, wherein at least some of the subsets of targets of different controllers from the subset of control molecules partially overlap one another by sharing one or more targets, to produce a biological effect through the modulation of the subset of targets. As a further example, a system being searched is selected from the group consisting of a living cell in an in-vitro culture, a computational representation of a biological system and an organism.

EXAMPLES

Example 1: Identification of a Kinase Inhibitor Subset as Control Molecules for Combinatorial Control of Biological Systems Combinatorial therapies based on kinase inhibitors offer an opportunity for implementing this proposed biomimetic strategy. There are 518 identified protein kinase genes in the human genome and they have been called the major drug targets of the twenty-first century, with thousands of inhibitors at different stages of development, mainly for cancer therapy, but also for other applications as inflammatory diseases. It is possible to characterize the target specificity of the inhibitors, for example by using panels of kinases (15), and inhibitors are available with different degrees of specificity. We therefore have the opportunity to experimentally test the use of pharmacological sets with parameters similar to those used in nature.

Obtaining a library of kinase inhibitors with characterized target specificity. Large, well-characterized libraries of small bioactive compounds and biomolecules, including kinase inhibitor libraries, available to different extents both in academia and industry, could also be sampled in such a way that the controller-target network of the resulting Biomimetic Set contains many or all of the desired biomimetic properties, as explained in the following steps.

Sampling a biomimetic Control Set from a larger library of kinase inhibitors. We have obtained from biological network datasets an estimate of the size of the biological controller sets as 8% of the size of the target sets. Considering the inhibitors as controllers and the set of all kinases as targets, this suggests a biomimetic control set of 40-60 kinase inhibitors (about 8% of 518) as a starting point. Optimal values for the other quantitative set parameters can be similarly estimated.

Given a large enough library of kinase inhibitors with characterized protein kinase targets (similarly we could use microRNAs with computationally predicted targets, or any other fully characterized library of targeted molecular agents), it is possible to construct a set of control molecules with target network properties similar to those seen in biological systems.

Network properties shown to be conserved in biological systems include but are not limited to:
  Size of the set of control molecules, as a percentage of the size of the target set (sometimes referred to as "M/N" in the above text)
  Number of interactions between control molecules and targets, as a percentage of all possible interactions (sometimes referred to as "link density" or "density" in the above text")
  Average amount of overlap of each set of targets with any other set of targets (sometimes referred to as "pairwise overlap" or "overlap" in the above text)
  Link distribution of interacting controllers per target molecule (sometimes referred to as "incoming link" or "$k_{in}$" distribution in the above text)
  Link distribution of interacting targets per controller molecule (sometimes referred to as "outgoing link" or "$k_{out}$" distribution in the above text)

These properties were measured for several biomolecular networks in three different organisms, as described in (1).

Using a published dataset of protein kinase targets of publicly available kinase inhibitors (15) in a simulation, a small Biomimetic Set of kinase inhibitors was extracted with size (M/N) and controller per target distribution similar to the biological networks inspected (1). Therefore, controller sets with the above biomimetic network properties can be built from larger molecular libraries, if given detailed target profiles for each compound.

Biological information can be applied in the design of the biomimetic Control Set. Most biological systems of interest, even those in which doctors or scientists cannot control the behavior, have been well studied, resulting in a wealth of available biological information. Biomimetic Sets can be constructed in a way that incorporates this information while constraining the network properties as indicated above.

Prior to sampling a large library of kinase inhibitors, all 518 protein kinase targets in the genome can be ranked according to importance in the in vitro disease model (cell line) of interest. In this example, the list of kinases can be ordered according to:

Expression of kinase mRNA in microarrays of the cell line
  Mutation of the kinase gene in exon sequencing of the cell line
  Mutation of the kinase gene in exon sequencing of patients with the actual disease of interest Mutations in the cell line can be given highest priority, followed by primary cancer mutations, followed by the rest of the kinases in the genome ordered by gene expression levels in the cell line. Additional ranking criteria could include, but are not limited to, biological data suggesting involvement in biological process or pathology of interest, expression of surface markers from flow cytometry data, or protein phosphorylation activity.

Next, since the desired exponential distribution of controllers is monotonically decreasing, a discrete, specific number of incoming links (controllers) can be assigned to each kinase in the ranked list according to this distribution (FIG. 2). The number of control molecules per target molecule can in part be determined by prioritizing the targets using the biological information described above. For example, targets with higher biological priority can be assigned greater probability of being acted on by a larger number of control molecules. This distribution can define the number of incoming links to each of the targets.

Linear optimization can be applied to design the biomimetic Control Set. Once a desired controller per target distribution, controller set size, and ranked target list have been obtained, a Biomimetic Set can be sampled from a larger library using linear programming to choose the subset of controllers that best fit these constraints. A binary integer linear optimization problem can be constructed as follows:

For binary vector $x=\{x_1, x_2, x_3, \ldots, x_n\}$, minimize $$\sum_i x_i$$

subject to $Ax \geq b$ and $$\sum_i x_i > \frac{M}{N},$$

where A is the controller-target interaction matrix, x is a selection vector denoting whether the controller molecule is chosen for the Biomimetic Set, b is the desired biomimetic number of controllers for each target corresponding to the rows of A, and $$\frac{M}{N}$$

is the desired biomimetic ratio of controller set size to target set size. Using the drug-target network drawn from the inhibitor library to form matrix A and using any linear programming software, feasible solutions to this optimization problem can be obtained, resulting in a binary vector x which represents whether or not each drug in the library is selected for the control set.

Using search algorithms to sample an effective control subset of kinase inhibitors from the Biomimetic Control Set. The control subset to be found are analogous to the number of transcription factors or kinases expressed in a given cell type from the entire genomic repertoire. From expression data of multiple cell types, it was found that biological systems express a subset of approximately one-third of their genes (the controller set) to achieve the differentiated (controlled) state. From this it can be estimated that effective control subsets of kinase inhibitors are likely to be composed of about 15 inhibitors and this number can be used as a starting point for the search algorithms, which can however also identify subsets of different sizes after the search.

Combinatorial control of biological systems could be found by searching within the biomimetic sets for effective subsets. Evolution conducts a similar search using all controller molecules encoded in the genome, in order to find the optimal subsets to be expressed in a particular cell type. The many-to-many approach would require, rather than reject, nonspecific controller molecules, and may be more robust to acquired resistance and biological variability due to higher $<k_{in}>$ for targets. This approach would be modular—as in biological control—and therefore more efficient than the present practice of developing a different drug for each indication, because the same sets of molecules can be used to search for therapies for different complex diseases.

Searching within a Biomimetic set is made possible because of the emergence of high-throughput in vitro or in vivo search algorithms for efficiently optimizing large combinations of drugs from within candidate sets [20-23]. These algorithms are essential to overcome the exponentially growing possibilities of the combinatorial space. It is clearly not sufficient for the Biomimetic Sets to have an optimal network structure, and these methods permit an efficient search for the appropriate combination of component molecules in the biological system of interest.

A search (or optimization) algorithm takes a set of measured combinations as input, and from these then suggests new candidates to measure, thus exploring the combinatorial space without measuring it at every point. Search algorithms could include, but are not limited to, a stack sequential algorithm (2, 24) such as those used in the field of information theory and digital decoding, a gradient-based search, or biologically-inspired algorithms such as particle swarm optimization, ant colony optimization, or genetic algorithms (25).

The search for combination subsets from within the Biomimetic Set could be implemented in vitro or in vivo, using iterative tests in a biological model system, or computationally in simulations.

Figure 4:
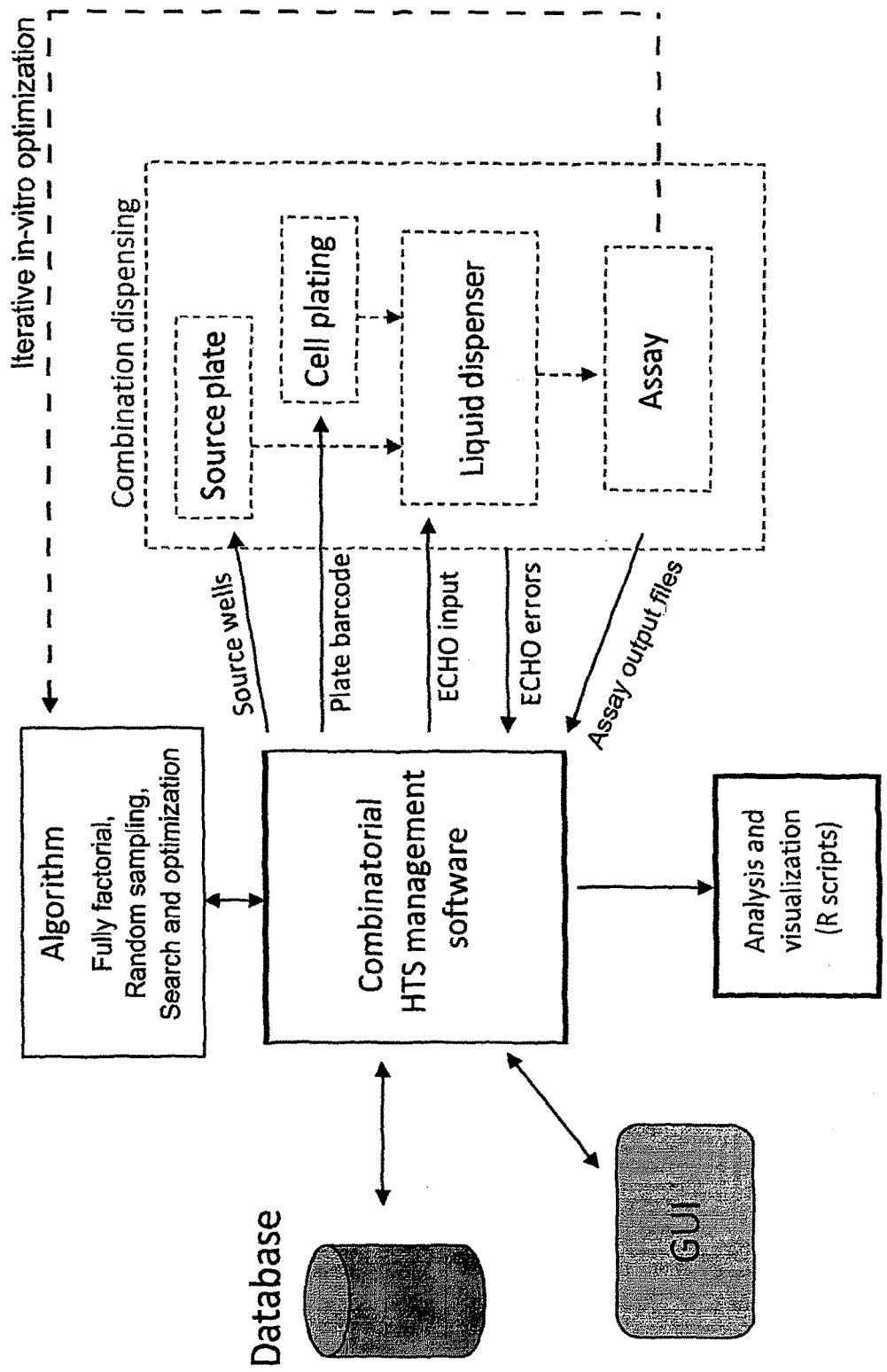
FIG. 4 depicts a schematic overview of a high-throughput combinatorial screening software platform. A database-backed custom software platform manages the design of combinations, exchange of files with the liquid handling and readout equipment, mapping of combinations to measured data, quality control, and compilation of screen results. The system is designed to generate fully factorial combinations (when all possible combinations can be measured), allow uploaded lists of candidate combinations, or implement search algorithms (including SS-TD, genetic algorithm and particle swarm optimization) for dynamically searching the experimental space over iterations of measurements.
Figure 6:
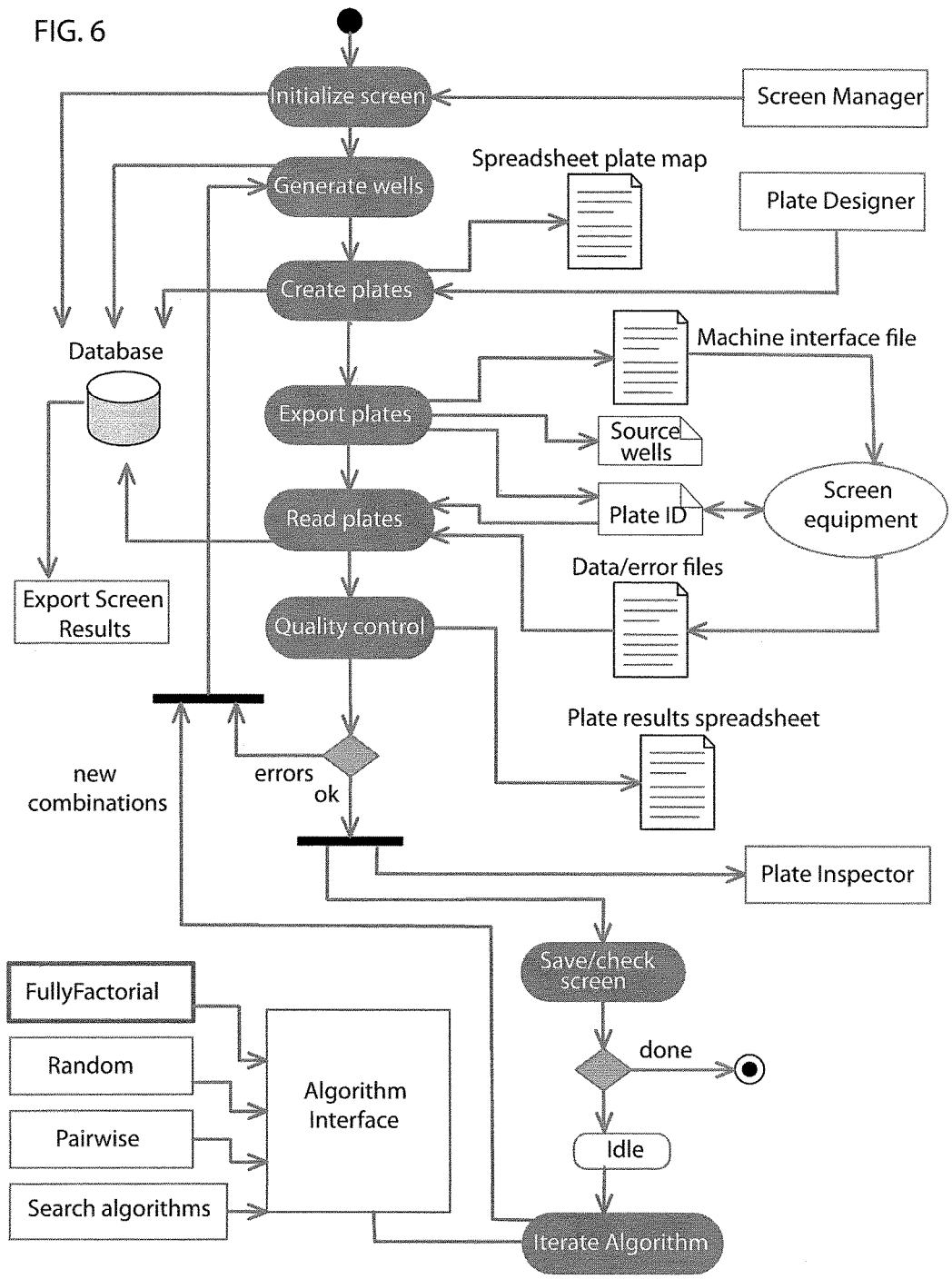
FIG. 6 depicts an activity diagram for an existing implementation of a computerized system for iterative search of the combinatorial space. A database (left) stores reagent identities, tracks reagent combinations dispensed in wells of a series of multiwell plates, and stores assay data measured for each combination. During the process (center) of performing an iterative screen, a computer program manages the generation of plate maps and files for interfacing screening equipment such as liquid handlers and plate readers. An interface allows user input throughout the process.

Biological, statistical and modeling information can be used to assist the search for effective controller subsets (2, 24). The number of control molecules per target molecule can in part be determined by prioritizing the targets using this biological information. This distribution can define the number of incoming links to each of the targets An in vitro search could use iterations of dispensing drug combinations and measuring the effect, then feeding the results back into an algorithm to optimally suggest new candidates to test, as described in (24). In a high-throughput implementation of this method, the combination dispensing could be done in multiwall plates using an acoustic liquid handler, and the output measurement (for example a cell viability measure) could be gathered by a luminescent or fluorescent plate reader. Specialized software can help to manage the algorithm, screening data, and liquid handler during the search process. A system for high-throughput combinatorial screening and search has been built and tested and is described in FIG. 4.

If the search is conducted using cancer and non cancer cell lines the biomedical effect can be selective killing of one or more cancer cell lines.

Although the above demonstrates exemplary embodiments including those directed towards the determination of a subset of kinase inhibitor molecules using kinases as the set of targets, the skilled artisan will appreciate that the approach can be extended to other classes of controllers (for example microRNAs or cytokines) and other types of biological effects (for example cell differentiation or resistance to hypoxia). The approach can also be extended to the concurrent use of more than one class of controller (for example kinase inhibitors and cytokines).

REFERENCES

1. Feala, J. D., Cortes, J., Duxbury, P. M., McCulloch, A. D., Piermarocchi, C., and Paternostro, G. 2010. Biological control networks suggest the use of biomimetic sets for combinatorial therapies. *Arxiv:*1006.0727.2204
2. Feala, J. D., Cortes, J., Duxbury, P. M., Piermarocchi, C., McCulloch, A. D., and Paternostro, G. 2009. Systems approaches and algorithms for discovery of combinatorial therapies. *WIREs Syst Biol Med*
3. Mayer, R. J. 2009. Targeted therapy for advanced colorectal cancer—more is not always better. *N Engl J Med* 360:623-625.19196680
4. Weinberg, R. A. 2007. *The Biology of Cancer*. New York: Garland Science.
5. DeVita, V. T., Lawrence, T. S., and Rosenberg, S. A. 2008. *DeVita, Hellman, and Rosenberg's cancer: principles &practice of oncology*. Philadelphia: Wolters Kluwer/Lippincott Williams & Wilkins. p. pp.
6. Ramaswamy, S. 2007. Rational design of cancer-drug combinations. *N Engl J Med* 357:299-300.17634467
7. Dancey, J. E., and Chen, H. X. 2006. Strategies for optimizing combinations of molecularly targeted anticancer agents. *Nat Rev Drug Discov* 5:649-659.16883303
8. Hopkins, A. L. 2008. Network pharmacology: the next paradigm in drug discovery. *Nat Chem Biol* 4:682-690.18936753
9. Zimmermann, G. R., Lehar, J., and Keith, C. T. 2007. Multi-target therapeutics: when the whole is greater than the sum of the parts. *Drug Discov Today* 12:34-42.17198971
10. Tol, J., Koopman, M., Cats, A., Rodenburg, C. J., Creemers, G. J., Schrama, J. G., Erdkamp, F. L., Vos, A. H., van Groeningen, C. J., Sinnige, H. A., et al. 2009. Chemotherapy, bevacizumab, and cetuximab in metastatic colorectal cancer. *N Engl J Med* 360:563-572.19196673
11. Sawyers, C. 2004. Targeted cancer therapy. *Nature* 432:294-297.15549090
12. Zhang, J., Yang, P. L., and Gray, N. S. 2009. Targeting cancer with small molecule kinase inhibitors. *Nature Reviews. Cancer* 9:28-39.1842
13. Frantz, S. 2005. Drug discovery: playing dirty. *Nature* 437:942-943.16222266
14. Mencher, S. K., and Wang, L. G. 2005. Promiscuous drugs compared to selective drugs (promiscuity can be a virtue). *BMC Clinical Pharmacology* 5:3-3.1846
15. Karaman, M. W., Herrgard, S., Treiber, D. K., Gallant, P., Atteridge, C. E., Campbell, B. T., Chan, K. W., Ciceri, P., Davis, M. I., Edeen, P. T., et al. 2008. A quantitative analysis of kinase inhibitor selectivity. *Nature Biotechnology* 26:127-132.2191

16. Barabasi, A. L., and Oltvai, Z. N. 2004. Network biology: understanding the cell's functional organization. *Nat Rev Genet.* 5:101-113.14735121
17. Jeong, H., Mason, S. P., Barabasi, A. L., and Oltvai, Z. N. 2001. Lethality and centrality in protein networks. *Nature* 411:41-42.11333967
18. Jeong, H., Tombor, B., Albert, R., Oltvai, Z. N., and Barabasi, A. L. 2000. The large-scale organization of metabolic networks. *Nature* 407:651-654
19. Ravasz, E., Somera, A. L., Mongru, D. A., Oltvai, Z. N., and Barabasi, A. L. 2002. Hierarchical organization of modularity in metabolic networks. *Science* 297:1551-1555.12202830
20. Stuart, J. M., Segal, E., Koller, D., and Kim, S. K. 2003. A gene-coexpression network for global discovery of conserved genetic modules. *Science* 302:249-255
21. Yook, S. H., Oltvai, Z. N., and Barabasi, A. L. 2004. Functional and topological characterization of protein interaction networks. *Proteomics* 4:928-942.15048975
22. Bhardwaj, N., Carson, M. B., Abyzov, A., Yan, K.-K., Lu, H., and Gerstein, M. B. 2010. Analysis of combinatorial regulation: scaling of partnerships between regulators with the number of governed targets. *PLoS Computational Biology* 6:e1000755-e1000755.2192
23. Newman, M. E. J., Strogatz, S. H., and Watts, D. J. 2001. Random graphs with arbitrary degree distributions and their applications. *Physical Review E* 64.2100
24. Calzolari, D., Bruschi, S., Coquin, L., Schofield, J., Feala, J. D., Reed, J. C., McCulloch, A. D., and Paternostro, G. 2008. Search algorithms as a framework for the optimization of drug combinations. *PLoS Comput Biol* 4:e1000249.19112483
25. Schneider, J. J., and Kirkpatrick, S. 2006. *Stochastic Optimization*: Springer.

What is claimed is:

1. A therapeutic method against a hematological cancer, the method comprising:
   a) providing a biological sample from blood or bone marrow of a patient suffering from a hematological cancer, the sample comprising cells;
   b) providing a plurality of control molecules as a set of control molecules, wherein each control molecule of the set is independently selected from the group consisting of a microRNA, a small molecule, a peptide, a protein, a cytokine, and a metabolite;
   c) isolating cancer cells using density gradient centrifugation;
   d) obtaining RNA sequence data from the cancer cells and selecting a subset of control molecules from a measure of enrichment in differentially expressed genes in groups including targets of the control molecules and their neighbors within a network model of intracellular interactions, wherein the enrichment in differentially expressed genes is measured by measuring and comparing RNA expression data of the cancer cells and the control cells;
   e) assaying the subset of control molecules with the cells using an endpoint assay to obtain a set of assay results for a biological effect, wherein the endpoint assay is selected from the group consisting of an assay that determines growth, survival, or death of a living cell or an assay that determines differentiation from one cell type to another cell type under in vitro testing conditions providing a significant correlation between the effects of the same drugs in vitro and in vivo;
   f) executing a software platform that manages design of combinations with an algorithm, exchanges files between liquid handling and plate readout equipment, maps combinations to measured data, and compiles results;
   g) searching with a liquid handler, multi-well plates and a plate reader, an experimental space over iterations of measurements;
   h) retrieving and storing files from a database to identify reagents, track reagent combinations dispensed in wells of a series of multi-well plates, maintain assay data measured for each combination, and generate plate maps and files for interfacing liquid handlers and plate readers while searching the experimental space;
   i) searching the set of assay results to identify a subset of control molecules, wherein
      i) the subset of control molecules is composed of at least three of the plurality of control molecules,
      ii) each of the control molecules of the subset binds at least three targets,
      iii) each of the at least three targets binds at least three of the control molecules in the subset, and
      iv) at least three of the control molecules of the subset bind to one or more shared targets, wherein a shared target is a target that binds at least two of the control molecules;
      further wherein each target is a molecule independently selected from the group consisting of a cellular protein, an RNA, and a metabolite;
   j) providing the identified subset of control molecules as contributing to a combinatorial therapy for a patient having a same hematological cancer; and
   k) administering the subset of control molecules to the patient.

2. The method of claim 1, wherein a size of the set of control molecules, as a percentage of the targets, is between 0.5% and 20%.

3. The method of claim 1, where a number of interactions between the control molecules of the subset and the targets, as a percentage of all possible interactions between control molecules and targets, is between 0.1% and 10%.

4. The method of claim 1, wherein an average percentage of overlap between a first set of targets with another set of targets is between 0.1% and 10%.

5. The method of claim 1, wherein a number of control molecules of the subset per target follows a monotonically decreasing distribution, optionally comprising an exponential or power-law distribution.

6. The method of claim 5, wherein the number of control molecules of the subset per target is determined by prioritizing the targets using biological information.

7. The method of claim 1, wherein a number of targets per control molecule of the subset follows a monotonically decreasing distribution, optionally comprising an exponential or power-law distribution.

8. The method of claim 1, wherein the a majority of the targets are protein kinases or mRNA molecules.

9. The method of claim 1, wherein each target is a protein kinase.

10. The method of claim 1, wherein targets are a set of targets selected from the group consisting of a set of protein kinases, protein phosphatases, proteases, microRNAs, and metabolic enzymes.

11. The method of claim 1, wherein the biological sample is obtained by a same patient as the use of the combinatorial therapy, thereby optimizing the combinatorial therapy for an individual patient.

12. The method of claim 1 where a size of the subset of control molecules as a percentage of a size of targets is between 0.3% and 10%.

13. The method according to claim 1, wherein the subset of control molecules are kinase inhibitors.

14. The method of claim 1, where the set of control molecules are component of cell culture media used for testing and are optimized to provide the biological effect of a statistically significant correlation of the response to the same drugs in vitro and in vivo.

15. The method of claim 1, where the step of searching the set of assay results further comprises molecular profiling of the cancer cells and clustering of patient subpopulations.

\* \* \* \* \*